(12) United States Patent
Weasler et al.

(10) Patent No.: US 10,932,754 B2
(45) Date of Patent: Mar. 2, 2021

(54) SYSTEMS FOR A WATER COLLECTION ASSEMBLY FOR AN IMAGING CABLE

(71) Applicant: General Electric Company, Schenectady, NY (US)

(72) Inventors: Marc N. Weasler, West Bend, WI (US); Daniel E. Bozich, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 242 days.

(21) Appl. No.: 16/115,485

(22) Filed: Aug. 28, 2018

(65) Prior Publication Data

US 2020/0069286 A1 Mar. 5, 2020

(51) Int. Cl.
*H02G 15/00* (2006.01)
*A61B 8/00* (2006.01)
*A61B 8/12* (2006.01)

(52) U.S. Cl.
CPC .............. *A61B 8/4422* (2013.01); *A61B 8/12* (2013.01)

(58) Field of Classification Search
CPC ........... A61B 8/4422; A61B 8/12; A61B 8/44; A61B 8/00; A61B 8/46; H02G 9/00; H02G 9/02; H02G 7/04
USPC ........ 174/68.1, 68.3, 135, 72 A, 74 R, 72 R, 174/88 R; 600/459, 437
See application file for complete search history.

(56) References Cited

U.S. PATENT DOCUMENTS

| | | | |
|---|---|---|---|
| 6,035,587 A | 3/2000 | Dressler | |
| 7,246,895 B2 | 7/2007 | Jones et al. | |
| 7,614,185 B2 | 11/2009 | Brochu | |
| 8,001,729 B2 * | 8/2011 | Joly, Jr. ................. | E04D 13/076 52/12 |
| 8,791,396 B2 * | 7/2014 | Burns .................... | C10G 1/008 219/542 |
| 10,363,014 B1 * | 7/2019 | Steinberg ............. | A61B 8/4444 |
| 10,480,193 B2 * | 11/2019 | Brochu ................ | E04D 13/076 |
| 10,505,311 B2 * | 12/2019 | Al-Ali ................ | A61B 5/04286 |
| 10,788,391 B2 * | 9/2020 | Lin .......................... | G01M 3/02 |
| 10,820,886 B2 * | 11/2020 | Son ..................... | A61B 8/4444 |
| 10,834,878 B2 * | 11/2020 | Morikoshi ........... | A01G 25/023 |

* cited by examiner

*Primary Examiner* — Angel R Estrada
(74) *Attorney, Agent, or Firm* — McCoy Russell LLP (57) ABSTRACT

Various methods and systems are provided for a water collection feature of an imaging probe assembly. In one example, a medical imaging probe assembly includes an electrical connector, an imaging probe, and an electrical cable including a first end connected to the electrical connector and a second end coupled to the imaging probe, the cable including a water collection feature arranged at an outer surface of the cable, proximate to the first end. The water collection feature may have converging edges extending outward from the cable, toward the first end, shaped to draw water droplets away from the cable.

20 Claims, 5 Drawing Sheets

SYSTEMS FOR A WATER COLLECTION ASSEMBLY FOR AN IMAGING CABLE

FIELD

Embodiments of the subject matter disclosed herein relate to cables of imaging probes, particularly ultrasound probe cables.

BACKGROUND

Imaging systems, such as those for medical applications, often include a base unit containing various electronics (such as a control system, display, and the like) and one or more cables for imaging probes that may be removably coupled to the base unit through an electrical connector of the cable. For example, ultrasound systems may utilize an ultrasound probe assembly which includes an electrical cable with a first end having an ultrasound transducer (e.g., probe) and a second end having an electrical connector. The electrical connector is adapted to couple to a base unit or control system of the ultrasound assembly in order to transfer electrical signals between the ultrasound transducer and the base unit. The probe cables may have varying lengths in order to be able to reach a patient during scanning. After scanning is complete, the probe end (e.g., the end of the assembly that includes the ultrasound transducer) may be cleaned and then hung or set aside to dry prior to a subsequent scanning session.

BRIEF DESCRIPTION

In one embodiment, a medical imaging probe assembly comprises, an electrical connector; an imaging probe; and an electrical cable including a first end connected to the electrical connector and a second end coupled to the imaging probe, the cable including a water collection feature arranged at an outer surface of the cable, proximate to the first end, the water collection feature having converging edges extending outward from the cable, toward the first end, and shaped to draw water droplets away from the cable.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 2-9 are shown approximately to scale, although other relative dimensions may be used, if desired.

DETAILED DESCRIPTION

Figure 2:
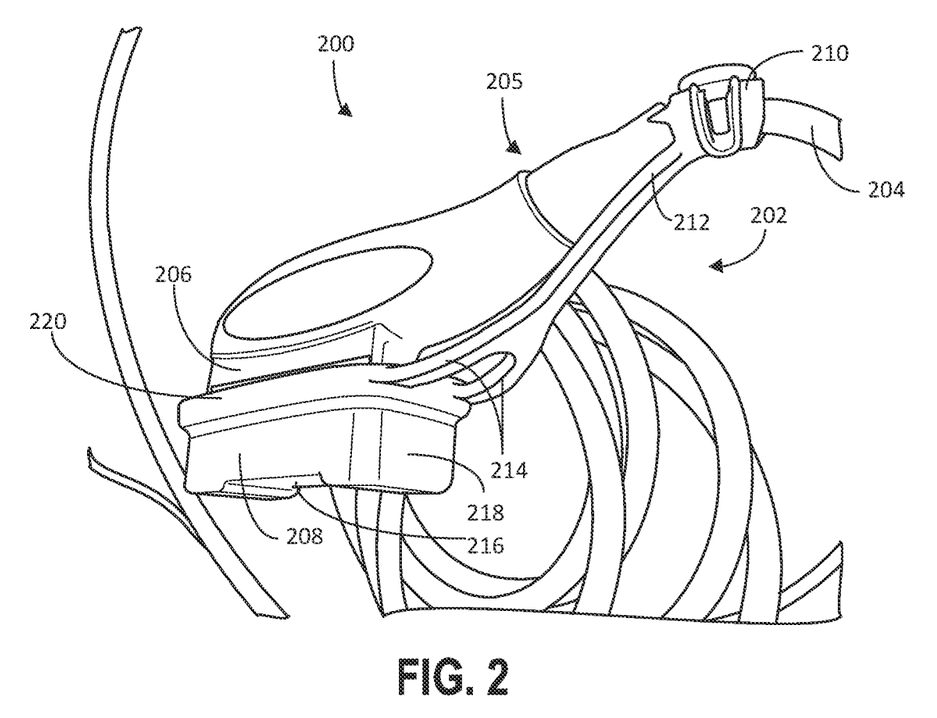
FIGS. 2-3 show a cover and water collection assembly coupled to an ultrasound probe assembly.
Figure 3:
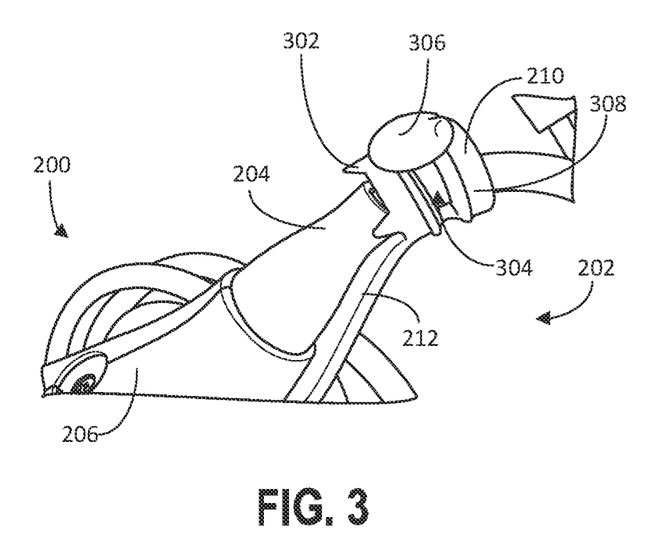
Figure 8:
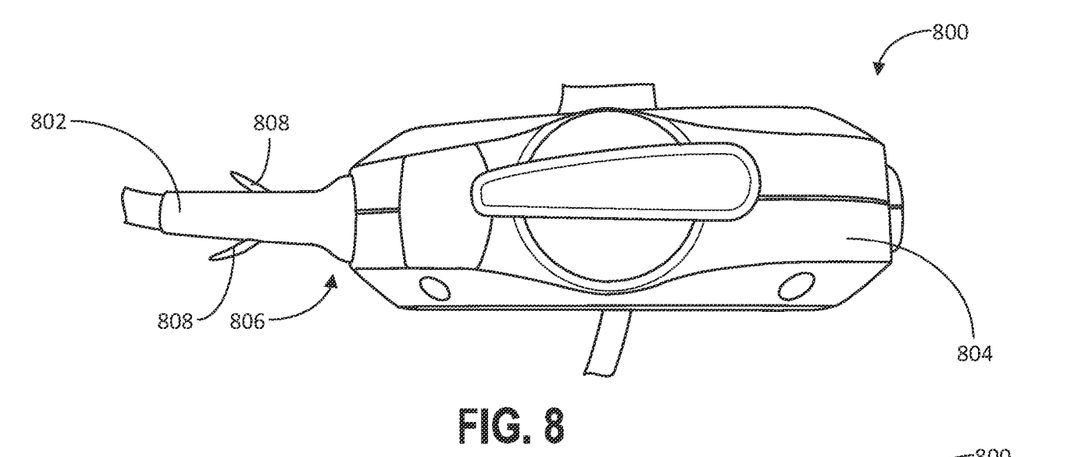
FIGS. 8-9 shows an embodiment of an imaging probe assembly having an electrical cable with water collection features integrated with the cable.
Figure 9:
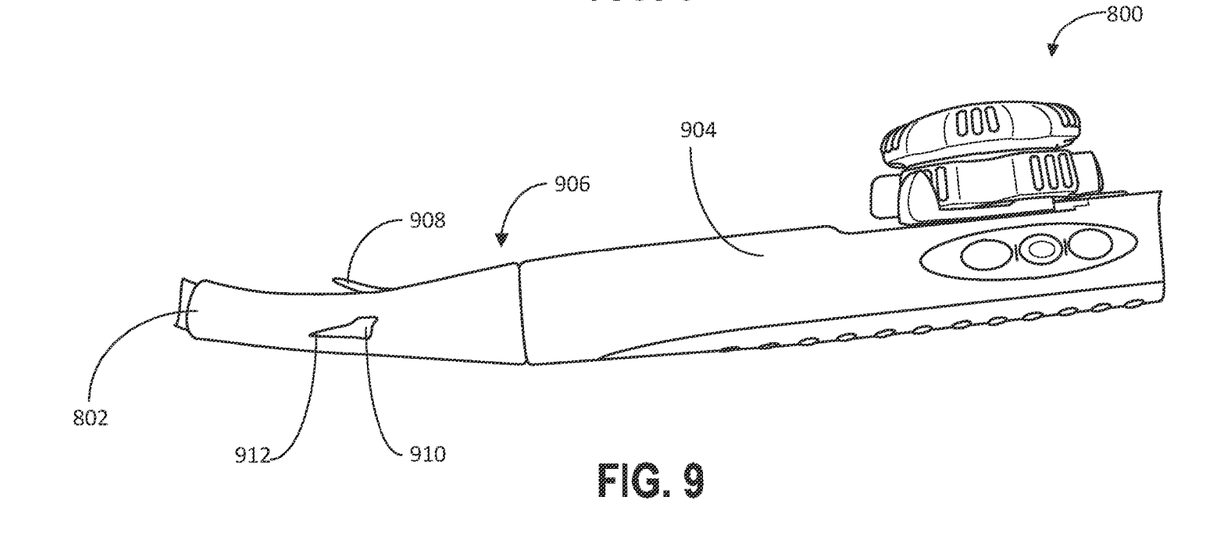

The following description relates to various embodiments of a water collection feature for an imaging probe assembly. Imaging systems, such as the imaging system shown in FIG. 1, may include a base unit containing various electronics (such as a control system, display, and the like) and one or more imaging probe assemblies removably coupled to the base unit. The imaging probe assembly may include an electrical cable with an electrical connector at a first end and an imaging probe at a second end, where the electrical connector is adapted to removably, electrically couple to the base unit. The imaging probe assembly may be exposed to water and/or cleaning fluids (e.g., during cleaning, following an imaging procedure) and may then be hung or set on a shelf before or after being cleaned. The water and/or cleaning fluids may run down the cable of the imaging probe assembly and come into contact with the electrical contacts of the electrical connector. This may result in corrosion of the electrical contacts and/or degradation of the imaging system when a wet electrical connector is plugged into the base unit. Thus, a water collection assembly including one or more water collection features that are shaped to draw water droplets away from the cable may be coupled to an exterior of the cable of the imaging probe assembly, as shown in FIGS. 2-3. In one embodiment, as shown in FIGS. 2-7, the water collection assembly may include a strap adapted to wrap around a circumference of an outer housing of the cable, the strap including one or more water collection features (e.g., drip points) shaped to draw water away from the cable and form water droplets that may release from narrowed (e.g., pointed) ends of the water collection features. In another embodiment, as shown in FIGS. 8-9, the water collection features may be directly coupled with (and/or integrated together with) an outer housing of the cable. In this way, water may be directed away from the cable and degradation of the electrical connector may be reduced.

Figure 1:
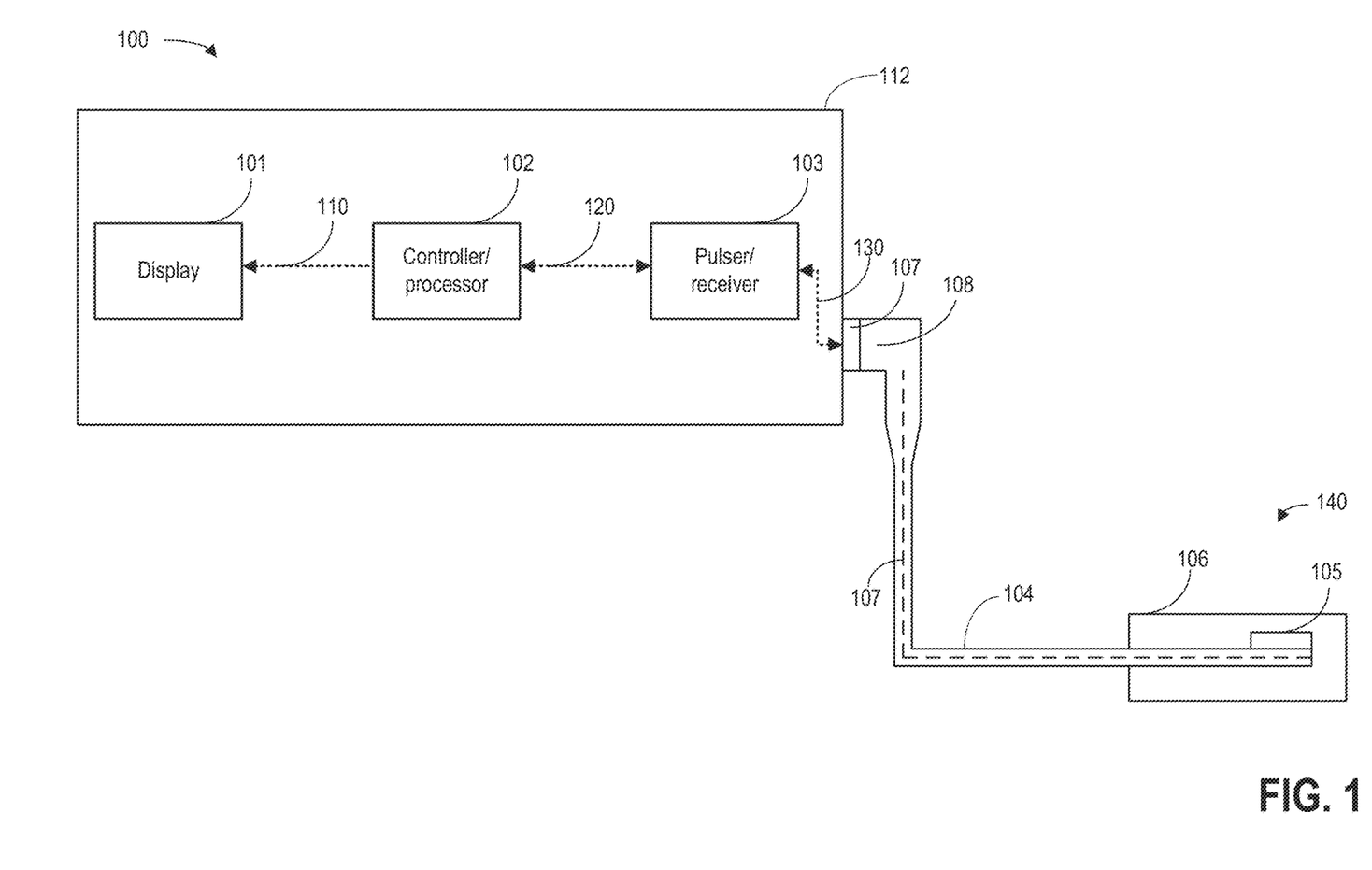
FIG. 1 shows an example imaging system, in the form of an ultrasound system, including an imaging probe assembly.

FIG. 1 is a schematic diagram of an imaging system 100 in accordance with an embodiment of the disclosure. In the example shown in FIG. 1, the imaging system 100 is an ultrasound imaging system. However, in alternate embodiments, the imaging system 100 may be a different type of imaging system such as a portable x-ray system.

System 100 includes a base unit 112 that includes the electronic display and control elements of the ultrasound imaging system. For example, base unit 112 may include an imaging console that may be moved around (e.g., rolled) a room or building by a user. As shown in FIG. 1, the base unit 112 includes a display module 101, a controller/processor 102, a pulser/receiver 103, and an electrical input connector 107. An ultrasound probe assembly 140 is connected to the electrical input connector 107 of the base unit 112 via an electrical connector 108 of the ultrasound probe assembly 140. In this way, electrical signals may be transferred between the ultrasound probe assembly 140 and the base unit 112 via the removable electrical connection between the electrical input connector 107 and electrical connector 108. The electrical connector 108 may be plugged into the electrical input connector 107 prior to and during an imaging procedure and then may be unplugged (e.g., uncoupled or removed) from the electrical input connector 107, following the imaging procedure, for cleaning and/or storage. The base unit 112 may include a plurality of electrical input connectors, similar to electrical connector 107, for coupling electrically to various imaging probes.

The dashed lines (110, 120, and 130) indicate communication of electrical signals between system components. The ultrasound probe assembly 140 includes the electrical connector 108, a cable 104, and an ultrasound probe 106 including an ultrasound transducer 105 mounted on a distal end of the cable 104, inside a housing of probe 106. The transducer generates acoustic signals and receives reflected acoustic signals. The cable 104 may be a coaxial cable that can rotate relative to its longitudinal axis 107 so that a plane perpendicular to the longitudinal axis of the probe may be imaged (e.g., the cable may have a rotational axis that is parallel to and aligned with the longitudinal axis of the probe). The ultrasound transducer 105 may be a single element transducer or an array of transducers. The cable 104 includes a first end directly coupled to the electrical connector 108 and a second end directly coupled to the ultrasound probe (e.g., imaging probe) 106. The cable 104 may be of various lengths and may be sized in order to reach a patient positioned away from the base unit 112.

Pulser/receiver 103 is controlled by controller/processor 102 for generating a high voltage pulse to ultrasound probe assembly 140. Acoustic signals reflected to the ultrasound probe 106 from the imaged object are converted into electrical signals and transmitted back to the pulser/receiver 103. The pulser/receiver 103 may also amplify the received electrical signals from the probe 106. The received electrical signals are further transmitted to the controller/processor 102 via electrical connection 120. An image or map of the imaged object is constructed based on the received electrical signals and displayed on display 101 and/or stored in memory of the controller/processor 102.

In another embodiment, the probe may include an array of ultrasound transducers, and can image or sense a plane or a volume without rotating cable 104.

FIGS. 2-9 show various embodiments of a water collection feature (which may be a drip point feature or assembly, in an embodiment) for an imaging probe assembly, such as the imaging probe assembly 140 shown in FIG. 1. Specifically, FIGS. 2-7 show embodiments of a cover and water collection assembly, which may include or be referred to as a drip point assembly, 202 and FIGS. 8-9 show an embodiment of an imaging (e.g., ultrasound) probe assembly including one or more water collection features (e.g., drip points) integrated into the cable.

Turning first to FIGS. 2-7, FIGS. 2-3 show a cover and water collection assembly (e.g., drip point assembly) 202 coupled to an ultrasound probe assembly 200 and FIGS. 4-7 shows different views of a cover and water collection assembly 402 adapted to be coupled to an ultrasound probe assembly, such as the ultrasound probe assembly 200 of FIGS. 2-3. The cover and water collection assembly 402 of FIGS. 4-7 may include similar features to that of the cover and water collection assembly 202 of FIGS. 2-3. Thus, similar parts between the two embodiments have been numbered with common reference numbers. Additionally, ultrasound probe assembly 200 may be similar to ultrasound probe assembly 140 shown in FIG. 1 and may be adapted to couple to base unit of an imaging system, such as system 100 shown in FIG. 1.

As shown in FIGS. 2-3, the ultrasound probe assembly 200 includes a cable (e.g., electrical cable) 204 and electrical connector 206. Specifically, cable 204 includes a first end 205 connected to the electrical connector 206 and a second end (not shown in FIGS. 2-3) coupled to an imaging probe, such as ultrasound probe 106 shown in FIG. 1. Cable 204 may have varying lengths and is shown coiled into a bundle in FIGS. 2-3. The cover and drip point assembly 202 is shown coupled (e.g., directly coupled) to the ultrasound probe assembly in FIGS. 2-3. However, the cover and drip point assembly 202 is adapted to be removably coupled to the ultrasound probe assembly 200, as explained further below.

The cover and drip point assembly 202 includes a connector cover 208, a strap 210, and a tether 212. The cover 208 is shaped to couple with and fit over the electrical connector 206, as shown in FIG. 2. Specifically, the cover 208 includes a bottom wall (e.g., base) 216 and four side walls 218 which form an inner cavity (not visible in FIG. 2) of the cover 208. The inner cavity is shaped to receive and couple around outer walls (e.g., surfaces) of the electrical connector 206. Each of the four side walls 218 are connected to the bottom wall 216. Additionally, the cover 208 includes an outer, top edge 220 connected to each of the four side walls 218 and arranged around an outer perimeter of cover 208, at an opposite end of the cover 208 from the bottom wall 216.

Figure 4:
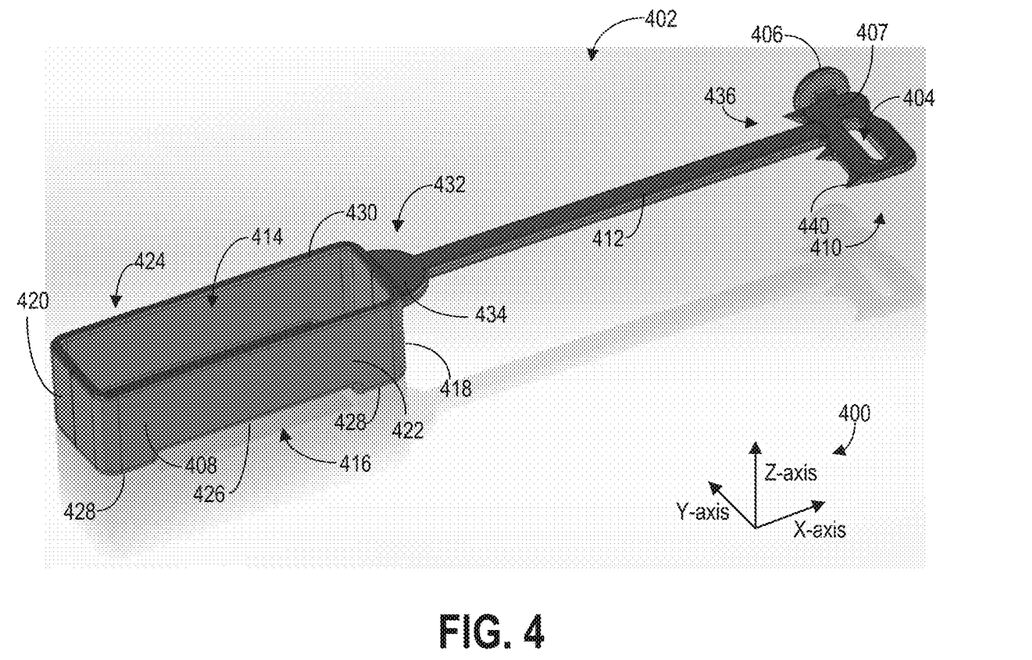
FIG. 4 shows a perspective view of a cover and water collection assembly for an imaging probe assembly.

In this way, electrical contacts on a bottom surface of the electrical connector 206 are completely covered by the cover 208 when the cover 208 is coupled with the electrical connector 206. Further, the side walls 218 and bottom wall 216 of the cover 208 may be size such that they form a fluid-tight connection with the electrical connector 206. For example, at least a portion of internal surfaces of one or more of the side walls 218 (as shown in FIG. 4) may be in face-sharing contact with the electrical connector 206 when the cover is positioned over and coupled to the electrical connector 206. As a result, the cover 208 prevents water or cleaning solution on or around the ultrasound probe assembly 200 (such as during a cleaning operation or when hanging to dry after being washed) from coming into contact with the electrical contacts of the electrical connector 206. This may reduce corrosion and degradation of the electrical connector 206, thereby increasing a longevity of the electrical connector 206.

Returning to FIG. 2, a first end of the tether 212 is directly connected to one side (e.g., a shorter side) of the top edge 220 of the cover 208. Specifically, the first end of the tether 212 includes a forked portion 214 including two arms that each couple directly to the outer, top edge 220 of the cover 208. The two arms of the forked portion 214 join together a distance along the tether 212 from the first end. A second end of tether 212 is directly connected to the strap 210. As shown in FIGS. 2-3, the strap is wrapped around an outer surface of the cable 204, around an entire circumference of the cable 204, proximate to the first end 205.

As shown in FIG. 3, the strap 210 includes a body 308 with an elongate aperture 304 arranged therein, through an entire thickness of the body 308. The strap 210 also includes a fastener 306 extending outward from the body 308. In FIGS. 2-3, the fastener 306 is shown threaded through the elongate aperture 304 and secured against an outer surface of the body 308, over the elongate aperture 304. In this way, the fastener 306 and elongate aperture 304 are secured together in order to secure the strap 210 around the cable 204. An embodiment of the cover and water collection assembly, similar to the cover and water collection assembly 200 shown in FIGS. 2-3, disconnected from the cable (where the fastener is not threaded through the elongate aperture) is shown in FIGS. 4-7, as described further below.

The second end of the tether 212 is directly coupled to a first edge of the body 308. Additionally, one or more water collection features 302 are directly connected to the first edge of the body 308. The water collection features 302 may be, in one example, drip points 302. The strap 210 includes three water collection features 302 (only two are visible in FIG. 3) spaced apart from one another along the first edge of the body 308. Each of the water collection features 302 has converging edges that extend outward from the cable 204, toward the first end 205, and are shaped to draw water droplets away from the cable 204 and form water droplets that are small enough to release from the converged ends of the water collection features. For example, as shown in FIGS. 2-3, the water collection features 302 may be drip points that have a wide end that narrows (e.g., converges) to a narrower end that may be pointed in shape. Water droplets may release from this narrower, pointed end, away from the cable 204. Further details on the shape of the water collection features or drip points and the strap will be discussed below with reference to FIGS. 4-7. In alternate embodiments, each of the water collection features 302 may be arranged on an opposite side of the strap 210 and may extend outward from the cable 204, toward a second end of the cable connected to the imaging probe.

The cover and drip point assembly 202 may be removed and uncoupled from the ultrasound probe assembly 200 by unfastening the fastener 306 from the elongate aperture 304 and uncoupling (e.g., by pulling away from one another) the cover 208 from the electrical connector 206. An embodiment of the cover and drip point assembly, uncoupled from an imaging probe assembly, is shown in FIGS. 4-7, as described below.

Figure 5:
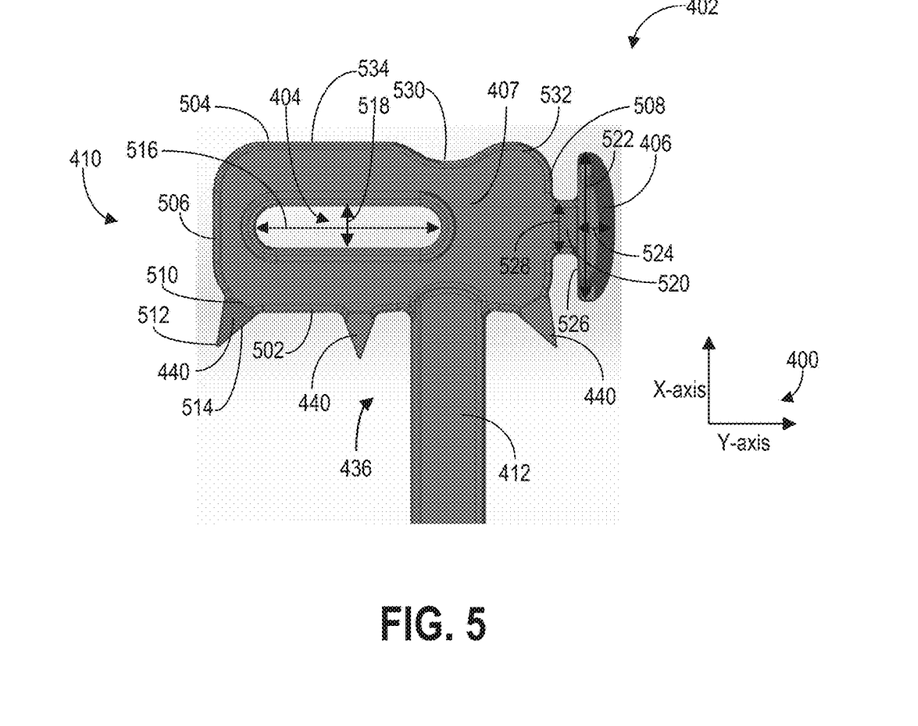
FIG. 5 shows a detailed top view of a strap of the cover and water collection assembly of FIG. 4.
Figure 6:
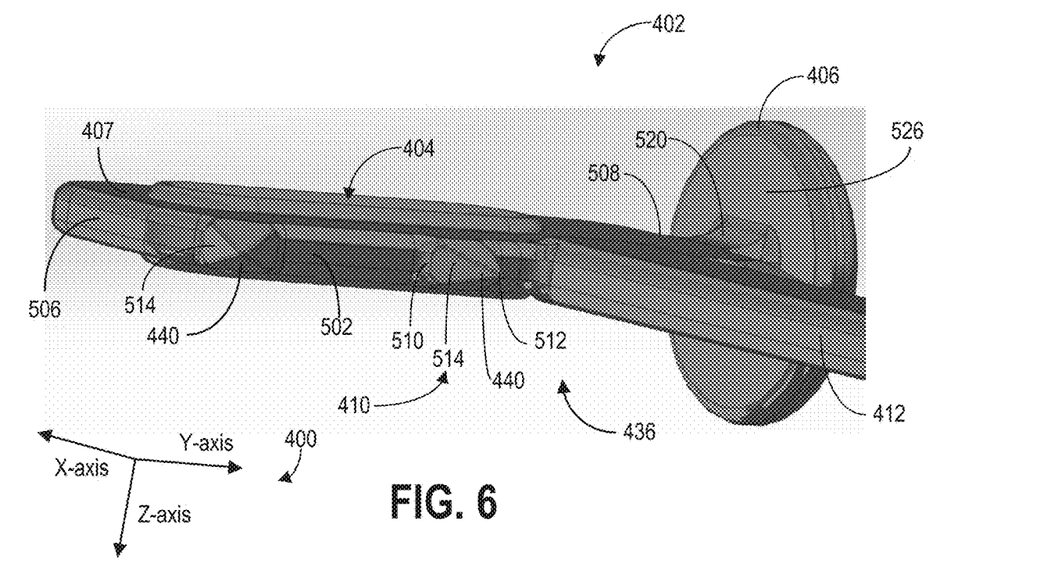
FIG. 6 shows a detailed side view of the strap of the cover and water collection assembly of FIG. 4.
Figure 7:
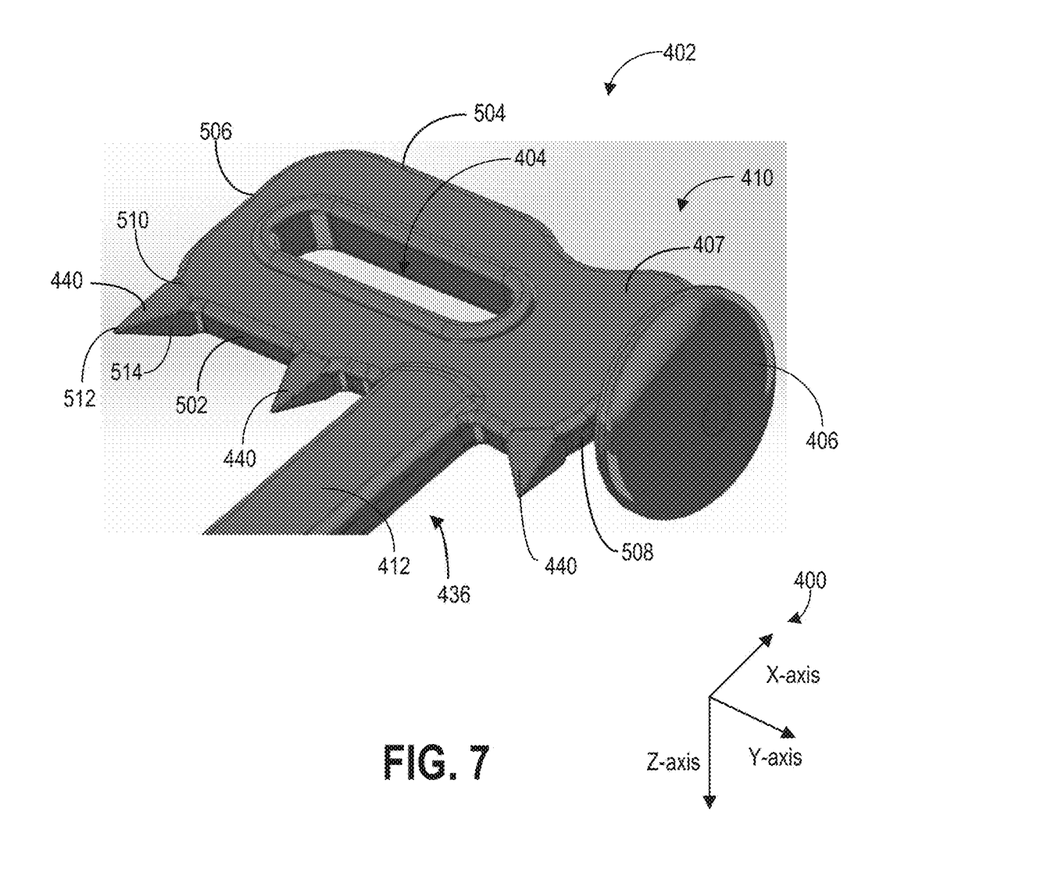
FIG. 7 shows a detailed perspective view of the strap of the cover and water collection assembly of FIG. 4.

FIGS. 4-7 show a second embodiment of a cover and water collection (e.g., drip point) assembly 402, which may be similar to the cover and drip point assembly 202 shown in FIGS. 2-3. Similar parts to the first embodiment of FIGS. 2-3 are numbered similarly in FIGS. 4-7. FIGS. 4-7 include reference axes 400, including an x-axis, y-axis, and z-axis. FIG. 4 shows a perspective view of the cover and drip point assembly 402, FIG. 5 shows a detailed top view of the strap 410 (similar to strap 210 shown in FIGS. 2-3) of the cover and drip point assembly 402, FIG. 6 shows a detailed side view of the strap 410, and FIG. 7 shows a detailed perspective view of the strap 410.

As shown in FIG. 4, the cover and drip point assembly 402 includes a cover (e.g., connector cover, which may be similar to cover 208 of FIG. 2) 408, a tether 412 (similar to tether 212 of FIGS. 2-3), and strap 410 (similar to strap 210 of FIGS. 2-3). The cover 408 is shaped to couple with and fit over an electrical connector of an imaging probe assembly (such as electrical connector 206 shown in FIG. 2). Specifically, the cover 408 includes a bottom wall (e.g., base) 416 and four side walls which form an inner cavity 414. The four side walls include first side wall 418, second side wall 420, third side wall 422, and fourth side wall 424, where the first and second side walls are shorter side walls, arranged opposite one another across the cavity 414, and the third and fourth side walls are longer side walls arranged opposite one another across the cavity 414. The bottom wall 416 includes a central, indented portion 426 which is depressed from planar, outer ends 428 of the bottom wall 416. As explained above with reference to FIGS. 2-3, the inner cavity 414 is shaped to receive and couple around outer walls (e.g., surfaces) of an electrical connector of an imaging probe assembly. Each of the four side walls 418, 420, 422, and 424 are connected to the bottom wall 416. Additionally, the cover 408 includes an outer, top edge 430 connected to each of the four side walls. The top edge 430 is arranged around an outer perimeter of the cover 408, at an opposite end of the cover 408 from the bottom wall 416, and forms an opening to the cavity 414.

A first end 432 of the tether 412 is directly connected to the first side wall 418 of the cover 208. Specifically, the first end 432 of the tether 412 includes a flared base 434, wider than a remainder of the tether 412, directly coupled to the first side wall 418. By having a flared base 434 that is wider than a remainder of the tether 412, the connection between the cover and tether may be more robust and less likely to become degraded over time. In the embodiment shown in FIG. 4, the flared base 434 is semi-circular in shape. However, in alternate embodiments, the flared base may have another shape. In some embodiments, the first end 432 of tether 412 may have a forked end, such as the tether 212 of FIG. 2.

A second end 436 of tether 412 is directly connected to the strap 410. The strap 410 is adapted to wrap around an entire circumference of an outer surface of a cable of an imaging probe assembly (such as cable 204 shown in FIG. 2). As shown in FIG. 4, the strap 410 includes a body 407 with an elongate aperture 404 arranged therein, through an entire thickness of the body 407. The strap 410 also includes a fastener 406 extending outward from the body 408. The second end 436 of the tether 412 is directly coupled to the body 408. Additionally, one or more water collection features 440 are directly connected to the body 408 and extend outward from the body 408. As shown in FIG. 4, the water collection features 440 have edges that converge and extend toward the cover 408. The water collection features 440 may be, in one example, drip points 440.

Turning to FIGS. 5-7, more detailed views of the strap 410 are shown. The body 407 of strap 410 has four sides or edges, including two long (e.g., longer) edges and two short (e.g., shorter) edges, the two long edges arranged substantially perpendicular to the two short edges. Specifically, body 407 includes a first long edge 502 arranged across a width (in the direction of the x-axis) of the body 407 of the strap 410 from a second long edge 504 and a first short edge 506 arranged across a length (in the direction of the y-axis) of the body 407 from a second short edge 508. The length of the body 407 (in the direction of the y-axis) is longer than the width of the body 407 (in the direction of the x-axis) and sized to wrap around a circumference of an imaging probe cable. Additionally, the second long edge 504 includes a planar portion 534, a depressed portion 530, and a curved portion 532. The depressed portion 530 is arranged between the planar portion 534 and curved portion 532 and includes a depression that is depressed inward, toward a center of the body 407, from the planar portion 534 and curved portion 532. The depressed portion 530 is arranged across the width of the body 407 from where the second end 436 of the tether 412 couples to the first long edge 502 of the body 407.

The water collection features 440 are directly coupled to the first long edge 502. Specifically, the embodiment of strap 410 shown in FIGS. 4-7 shows three water collection features (e.g., drip points) 440 spaced apart from one another along the first long edge 502. However, in alternate embodiments, the strap 410 may include more or less than three water collection features 440 (such as two, four, or five). Further, in another embodiment, the water collection features 440 may be directly coupled to the second long edge 504 instead of the first long edge 502 and may extend outward from the second long edge 504 (toward an imaging probe end of the cable, when coupled around the cable). As shown in FIGS. 4-7, each water collection feature 440 extends outward from the first long edge 502, toward the second end 432 of the tether 412 and the cover 408. Specifically, each water collection feature 440 has a wider end 510 and a narrower end 512 spaced away from the first long edge 502 and pointing toward the cover 408. Each water collection feature 440 has edges 514 that converge (e.g., narrow) from the wider end 510 to the narrower end 512. In this way, the water collection features 440 are shaped to draw water droplets away from the cable (to which the body 407 is adapted to wrap around and contact when fastened).

As shown in FIGS. 6 and 7, each water collection feature 440 has four planar edges 514 that converge to the narrower end 512 which may be pointed (e.g., having a relatively sharp point). The point of the pointed, narrower end 512 creates a relatively small water droplet, thereby enabling the water collection features 440 to collect and remove water from the cable of the imaging probe assembly to which the strap 410 is coupled. For example, when the strap 410 is coupled around a cable of an imaging probe assembly (as shown in FIGS. 2-3), fluid running down the cable may contact the strap and the wider end 510 of a water collection feature 440. The converging edges 514 provide a pathway for fluid to run down to the narrower end 512, at which point a water droplet forms and then drips off the end of the water collection feature (e.g., drip point) 440), away from the electrical connector of the imaging probe assembly. Since the fluid on the cable has surface tension which makes it difficult to release from the cable, the water collection features on the strap (or on the cable itself, as discussed below with reference to FIGS. 8-9) breaks the surface tension and directs the fluid to a point (at the narrower end 512) where the fluid will release from the strap and cable.

The pointed, narrower end 512 may have a slight radius (for manufacturability, in one example) which may be approximately 30 thousandths in one example. In alternate examples, this radius may be in a range of 20-40 thousandths. In yet another example, this radius may be in a range of 25-60 thousandths. Each of the edges 514 is triangular in shape and there may be a rounded or chamfered edge between adjacent edges 514 of the same water collection feature 440. Though each water collection feature 440 is shown having four edges 514, in alternate embodiments each water collection feature may have more or less than four edges 514 (such as three, five, or six).

As shown in FIGS. 5 and 7, the second end 436 of tether 412 is directly coupled to the first long edge 502, between two adjacent water collection features 440. A width of the tether (in the direction of the y-axis) is wider than a width of the wider end 510 of each water collection feature 440.

The elongate aperture 404 is arranged in the body 407, closer to the first short edge 506 than the second short edge 508. The elongate aperture 404 is oval-shaped having a length 516 and width 518, the width 518 defined as a diameter of circular ends of the elongate aperture 404, the width 518 smaller than the length 516. The elongate aperture 404 is approximately centered along a width of the body 407, between first long edge 502 and second long edge 504, in the direction of the x-axis.

The elongate aperture 404 is spaced away from the fastener 406. As shown in FIGS. 5 and 6, the fastener 406 is connected to the second short edge 508 via a stem 520. The stem 520, and thus the fastener 406, extends outward from the second short edge 508. As shown in FIGS. 4-7, the fastener 406 is button-shaped with a diameter 522 and height 524. The height 524 defines a highest point of the fastener 406 which extends and curves outward from a base 526 of the fastener 406. The stem 520 is directly connected to the base 526 at a center of the fastener 406. The dimeter 522 is smaller than the length 516 of the elongate aperture 404 and the height 524 is slightly smaller than the width 518 of the elongate aperture 404, so that the fastener 406 fits through the width 518 of the elongate aperture 404. In this way, the fastener 406 is adapted to be removably coupled with the elongate aperture 404. When the fastener 406 is inserted through and coupled with the elongate aperture 404, after wrapping the body 407 around a circumference of a cable of an imaging probe assembly (as shown in FIGS. 2-3), the base 526 is in face-sharing contact with a surface (between and defined by the four edges of body 407) of the body 407. The length 516 is longer than a width 528 of the stem 520 to allow the strap 410 to be wrapped around cables of varying outer diameter.

In the embodiments shown in FIGS. 2-7, the cover, strap, and tether are integrated together and formed as one piece. Additionally, the water collection features (e.g., drip points) are directly coupled to and integrated with the strap. In one example, the cover and water collection assemblies described herein are comprised entirely of silicone. For example, the cover and water collection assembly may be a silicone molded part and thus molded together as one piece.

However, in another embodiment, the water collection (e.g., drip point assembly) may be similar to the embodiments shown in FIGS. 2-7, but may not include the cover and tether. In this way, the drip point assembly may only include the strap adapted to wrap around the cable of the imaging probe assembly and collect and remove water droplets from the cable via the water collection features of the strap.

In yet another embodiment, as shown in FIGS. 8-9, the water collection features may be integrated with the cable of the imaging probe assembly. In this embodiment, the water collection features are directly coupled to and integrated with an outer housing of the cable, instead of a strap wrapped around the cable.

Turning to FIGS. 8-9, a medical imaging probe assembly 800 having an electrical cable 802 with water collection features 808 and 908 integrated with the cable 802 are shown. Specifically, FIG. 8 shows a first end of the imaging probe assembly 800 having an electrical connector 804 coupled to the cable 802 at a first end 806 of the cable 802. The cable 802 includes water collection features 808 directly coupled to the outer housing of the cable 802, around an outer circumference of the cable 802, proximate to the first end 806. The water collection features 808 extend outward and away from the outer housing of the cable 802, in a direction away from the connector 804. In one embodiment, the water collection features 808 are integrated with (e.g., molded together) with the outer housing of the cable 802. In this way, the water collection features may be formed during manufacturing of the cable.

FIG. 9 shows a second end of the imaging probe assembly 800 having a guiding device 904 coupled to an internal imaging probe (not show). A second end 906 of the cable 802 is coupled to guiding device 904. The second end 906 of cable 802 includes water collection features 908 directly coupled to the outer housing (e.g., surface) of the cable 802, around an outer circumference of the cable 802, proximate to the second end 906. In one embodiment, the water collection features 908 are integrated with (e.g., molded together) with the outer housing of the cable 802. In this way, the water collection features may be formed during manufacturing of the cable. The water collection features 908 include a wider end 910 directly connected to the cable 802 and a narrower end 912, forming a point, that extends away from the outer housing of the cable 802 and away from the guiding device 904.

The electrical cables of the imaging probe assemblies described herein may be for a variety of imaging probe assemblies having cables, including various types ultrasound imaging probe assemblies, portable x-ray detector assemblies, magnetic resonance coils, and the like.

FIGS. 1-9 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

In this way, a water collection assembly (also referred to herein as a drip point assembly) including one or more water collection features (e.g., drip points) may be used to direct water away from an imaging probe assembly (when coupled to an electrical cable of the imaging probe assembly), before water can reach an electrical connector of the imaging probe assembly. For example, each water collection feature may include a first, wider end directly connected to and integrated with either the outer housing of the cable or with a strap wrapped around an entire circumference of the cable and a second, narrower end that extends away from the cable. The narrower end may form a point which helps to break the surface tension of water traveling along the cable and form small enough water droplets that may be released from the water collection feature, before the water can come into contact with the electrical connector of the imaging probe assembly. As a result, this may reduce degradation and/or corrosion of the electrical contacts of the electrical connector, thereby increasing the longevity of the imaging probe assembly and reducing degradation of an imaging system to which the imaging probe assembly may be connected. Further, in some embodiments, when the water collection features are included on a strap adapted to wrap and fasten around a circumference of the cable, the strap may be additionally coupled to a connector cover via a tether. The connector cover is adapted to form a fluid-tight connection to the electrical connector, over the contacts of the electrical connector, thereby blocking fluid ingress into the connector and further reducing degradation of the electrical connector during and after cleaning of the imaging probe assembly. The strap, cover, and tether may be made of silicone and molded together as one piece, thereby increasing the ease of manufacturing the cover and drip point assembly. The technical effect of having an imaging probe assembly with an electrical cable including a first end connected to an electrical connector and a second end coupled to an imaging probe, the cable including a water collection feature arranged at an outer surface of the cable, proximate to the first end, the water collection feature having converging edges extending outward from the cable, toward the first end, and shaped to draw water droplets away from the cable, is to collect and direct water away from the cable and electrical connector, and form and release water droplets from the assembly, thereby reducing degradation of the electrical connector.

As one embodiment, a medical imaging probe assembly, comprises: an electrical connector; an imaging probe; and an electrical cable including a first end connected to the electrical connector and a second end coupled to the imaging probe, the cable including a water collection feature arranged at an outer surface of the cable, proximate to the first end, the water collection feature having converging edges extending outward from the cable, toward the first end, and shaped to draw water droplets away from the cable. In one example, the water collection feature is directly coupled to and integrated with an outer housing of the cable. For example, the water collection feature may include a wider, first end directly coupled to the outer housing and a narrower, converged second end arranged a distance away from the outer housing and pointing toward the electrical connector. In another example, the water collection feature is directly coupled to and integrated with a strap wrapped around an outer housing of the cable. For example, the water collection feature may include a wider, first end directly coupled to an edge of the strap and a narrower, converged second end arranged a distance away from the strap and pointing toward the electrical connector. Additionally or alternatively, the electrical cable includes a plurality of the water collection features spaced apart from one another around the outer circumference of the cable. In another example, the water collection feature has a triangular shape with a wide end arranged at the cable and a pointed end spaced away from and extending away from the cable. In yet another example, the water collection feature is comprised entirely of silicone.

As another embodiment, a drip point assembly for an electrical imaging cable of an imaging probe, comprises: a strap including a body with two long edges arranged perpendicular to and coupled to two short edges of the strap, a plurality of drip points spaced apart from one another along a first long edge of the two long edges and extending outward from the first long edge, an elongate aperture arranged in the body closer to a first short edge of the two short edges than a second short edge of the two short edges, and a fastener extending outward from the second short edge. The drip point assembly may additionally include a connector cover spaced away from the strap and connected to the first long edge of the strap via a tether, the connector cover including a cavity formed by four outer side walls and a bottom wall of the connector cover. In one example, the tether includes a first end directly coupled to the first long edge, between two adjacent drip points of the plurality of drip points and a second end directly coupled to an outer edge of the connector cover which forms an opening of the cavity. In another example, the strap, cover, and tether are integrated together and formed as one piece. In another example, the elongate aperture is oval-shaped having a length and width, the width defined as a diameter of circular ends of the elongate aperture, and wherein the fastener is button-shaped with a diameter that is smaller than the length of the elongate aperture and a height that is shaped to fit through the width of the elongate aperture. In still another example, the strap, including the plurality of drip points, is comprised entirely of silicone and wherein the elongate aperture is adapted to receive the fastener.

As yet another embodiment, a cover and drip point assembly for an electrical connector of an ultrasound probe assembly, comprises: a cover including a cavity shaped to removably couple with the electrical connector; a strap including a plurality of drip points arranged along a first edge of the strap, the first edge facing the cover; and a tether including a first end directly coupled to an outer edge of the cover and a second end directly coupled to the first edge of the strap. In one example, the strap further includes an elongate aperture positioned in a central region of the strap, between the first edge and an oppositely arranged second edge of the strap, and a fastener extending outward from a third edge of the strap, the third edge arrange perpendicular to each of the first and second edges. In another example, the first end of the tether is directly coupled to the first edge, between two adjacent drip points of the plurality of drip points, and the second end of the tether includes a forked portion including two arms that each couple directly to the outer edge of the cover. In yet another example, the cover, strap, and tether are molded together as one piece and comprised entirely of silicone. In another example, the cover includes a bottom wall and four outer side walls coupled between the bottom wall and the outer edge, the outer edge forming an opening of the cavity. In one example, each drip point of the plurality of drip points includes a wide end directly coupled to the first edge and a pointed end extending away from the first edge, toward the cover, and wherein the plurality of drip points are spaced apart from one another along the first edge.

In another representation, a medical imaging probe assembly comprises: an electrical connector; an imaging probe; and an electrical cable including a first end connected to the electrical connector and a second end coupled to the imaging probe, the cable including a water collection feature arranged at an outer surface of the cable. The water collection feature may be positioned between the first end and the second end. The water collection feature may have one or more points. The water collection feature may have converging edges extending outward from the cable and shaped to draw water droplets away from the cable. In a first example of the medical imaging probe assembly, the water collection feature is arranged closer to the first than the second end. In a second example of the medical imaging probe assembly, the cable additionally includes a guide feature arranged between the first end and the second end and the water collection feature may be additionally or alternatively arranged proximate to the guide feature. In a third example of the medical imaging probe assembly, the water collection feature extends toward the electrical connector. In a fourth example of the medical imaging probe assembly, the water collection feature extends away from the electrical connector and toward the second end of the cable.

In yet another representation, a water collection assembly for an electrical imaging cable of an imaging probe, comprises: a strap including a body with edges, at least one water collection feature extending outward from a first edge of the edges, an aperture arranged in the body, and a fastener extending outward from a second edge of the edges, where the fastener and aperture are shaped to mate with one another to tightly coupled the strap around the electrical imaging cable. In one example, the strap includes a plurality of the water collection features spaced apart from one another along the first edge. In another example, the water collection feature, or each water collection feature of the plurality of water collections features, has edges that converge as the water collection feature extends away from the first edge and is shaped to direct water away from the strap and electrical imaging cable which the strap is connected to and to form water droplets that detach from the converged edges of the water collection feature. In yet another example, the aperture is positioned in the body at a location that is spaced away from the second edge from which the fastener extends. In another example, the strap is composed entirely of a flexible material that is adapted to bend. The water collection assembly may further comprise a connector cover connected to the strap via a tether, where the connector cover, tether, and strap are integrated together as one piece.

In still another representation, a cover and water collection assembly for an electrical connector of an imaging probe assembly, comprises: a cover including a cavity shaped to removably couple with the electrical connector; a strap including a plurality of water collection features arranged along a first edge of the strap; and a tether including a first end directly coupled to the cover and a second end directly coupled to the first edge of the strap. The water collection features may be drip points that have edges that converge to a pointed portion, the pointed portion spaced away from the first edge. In one example, the first edge faces the cover. In another example, the first edge is arranged opposite to a second edge of the strap, the second edge facing the cover.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging probe assembly, comprising:
   an electrical connector;
   an imaging probe; and
   an electrical cable including a first end connected to the electrical connector and a second end coupled to the imaging probe, the cable including a water collection feature arranged at an outer surface of the cable, proximate to the first end, the water collection feature having converging edges extending outward from the cable, toward the first end, and shaped to draw water droplets away from the cable.

2. The assembly of claim 1, wherein the water collection feature is directly coupled to and integrated with an outer housing of the cable.

3. The assembly of claim 2, wherein the water collection feature includes a wider, first end directly coupled to the outer housing and a narrower, converged second end arranged a distance away from the outer housing and pointing toward the electrical connector.

4. The assembly of claim 1, wherein the water collection feature is directly coupled to and integrated with a strap wrapped around an outer housing of the cable.

5. The assembly of claim 4, wherein the water collection feature includes a wider, first end directly coupled to an edge of the strap and a narrower, converged second end arranged a distance away from the strap and pointing toward the electrical connector.

6. The assembly of claim 1, wherein the electrical cable includes a plurality of the water collection features spaced apart from one another around the outer circumference of the cable.

7. The assembly of claim 1, wherein the water collection feature has a triangular shape with a wide end arranged at the cable and a pointed end spaced away from and extending away from the cable.

8. The assembly of claim 1, wherein the water collection feature is comprised entirely of silicone.

9. A drip point assembly for an electrical imaging cable of an imaging probe, comprising:
   a strap including a body with two long edges arranged perpendicular to and coupled to two short edges of the strap, a plurality of drip points spaced apart from one another along a first long edge of the two long edges and extending outward from the first long edge, an elongate aperture arranged in the body closer to a first short edge of the two short edges than a second short edge of the two short edges, and a fastener extending outward from the second short edge.

10. The drip point assembly of claim 9, further comprising a connector cover spaced away from the strap and connected to the first long edge of the strap via a tether, the connector cover including a cavity formed by four outer side walls and a bottom wall of the connector cover.

11. The drip point assembly of claim 10, wherein the tether includes a first end directly coupled to the first long edge, between two adjacent drip points of the plurality of drip points and a second end directly coupled to an outer edge of the connector cover which forms an opening of the cavity.

12. The drip point assembly of claim 11, wherein the strap, cover, and tether are integrated together and formed as one piece.

13. The drip point assembly of claim 9, wherein the elongate aperture is oval-shaped having a length and width, the width defined as a diameter of circular ends of the elongate aperture, and wherein the fastener is button-shaped with a diameter that is smaller than the length of the elongate aperture and a height that is shaped to fit through the width of the elongate aperture.

14. The drip point assembly of claim 9, wherein the strap, including the plurality of drip points, is comprised entirely of silicone and wherein the elongate aperture is adapted to receive the fastener.

15. A cover and drip point assembly for an electrical connector of an ultrasound probe assembly, comprising:
   a cover including a cavity shaped to removably couple with the electrical connector;
   a strap including a plurality of drip points arranged along a first edge of the strap, the first edge facing the cover; and
   a tether including a first end directly coupled to an outer edge of the cover and a second end directly coupled to the first edge of the strap.

16. The assembly of claim 15, wherein the strap further includes an elongate aperture positioned in a central region of the strap, between the first edge and an oppositely arranged second edge of the strap, and a fastener extending outward from a third edge of the strap, the third edge arrange perpendicular to each of the first and second edges.

17. The assembly of claim 15, wherein the first end of the tether is directly coupled to the first edge, between two adjacent drip points of the plurality of drip points, and the second end of the tether includes a forked portion including two arms that each couple directly to the outer edge of the cover.

18. The assembly of claim 15, wherein the cover, strap, and tether are molded together as one piece and comprised entirely of silicone.

19. The assembly of claim 15, wherein the cover includes a bottom wall and four outer side walls coupled between the bottom wall and the outer edge, the outer edge forming an opening of the cavity.

20. The assembly of claim 15, where each drip point of the plurality of drip points includes a wide end directly coupled to the first edge and a pointed end extending away from the first edge, toward the cover, and wherein the plurality of drip points are spaced apart from one another along the first edge.

* * * * *